(12) United States Patent
Freiberg et al.

(10) Patent No.: US 10,448,960 B2
(45) Date of Patent: Oct. 22, 2019

(54) FEMORAL FINISHING GUIDE

(71) Applicant: Zimmer, Inc., Warsaw, IN (US)

(72) Inventors: Andrew Freiberg, Weston, MA (US); Lindsey R. Rolston, New Castle, IN (US); Jeffery A. VanDiepenbos, Syracuse, IN (US); Anthony Romano, Columbia City, IN (US); Nolan C. Jones, Warsaw, IN (US); Jason S. Toler, Pierceton, IN (US); Brian D. Earl, South Bend, IN (US)

(73) Assignee: Zimmer, Inc., Warsaw, IN (US)

(*) Notice: Subject to any disclaimer, the term of this patent is extended or adjusted under 35 U.S.C. 154(b) by 404 days.

(21) Appl. No.: 15/203,370

(22) Filed: Jul. 6, 2016

(65) Prior Publication Data
US 2017/0007273 A1    Jan. 12, 2017

Related U.S. Application Data

(60) Provisional application No. 62/189,416, filed on Jul. 7, 2015.

(51) Int. Cl.
*A61B 17/17* (2006.01)
*A61B 17/15* (2006.01)
*A61B 17/16* (2006.01)

(52) U.S. Cl.
CPC ........ *A61B 17/1764* (2013.01); *A61B 17/155* (2013.01); *A61B 17/16* (2013.01)

(58) Field of Classification Search
CPC ... A61B 17/17; A61B 17/1764; A61B 17/155; A61B 17/1675
See application file for complete search history.

(56) References Cited

U.S. PATENT DOCUMENTS 5,683,397 A * 11/1997 Vendrely .............. A61B 17/155
606/88
5,810,829 A * 9/1998 Elliott .................. A61B 17/155
606/80

(Continued)

FOREIGN PATENT DOCUMENTS

CN       107847233      3/2018
JP       2018519926     7/2018

(Continued)

OTHER PUBLICATIONS

"International Application Serial No. PCT/US2016/041137, International Search Report dated Sep. 12, 2016", 7 pgs.

(Continued)

*Primary Examiner* — Matthew J Lawson
(74) *Attorney, Agent, or Firm* — Schwegman Lundberg & Woessner, P.A.

(57) ABSTRACT

Methods and apparatuses including an apparatus for guiding a femoral bone cut during knee replacement surgery are disclosed. The apparatus can comprise a cut guide having a first side, a second side, a third side, and one or more slots. The first side can be configured to interface with a resected surface of a femur. The second side can be spaced from the first side. The one or more slots can be defined by the apparatus and extend from the first side to the second side. The third side can be disposed between the first side and the second side and can have at least one projection extending therefrom. The at least one projection can be configured to guide a cutting tool into the one or more slots.

14 Claims, 12 Drawing Sheets

(56) References Cited

U.S. PATENT DOCUMENTS

| | | | |
|---|---|---|---|
| 2003/0225413 A1* | 12/2003 | Sanford | A61B 17/155 606/87 |
| 2004/0153086 A1* | 8/2004 | Sanford | A61B 17/155 606/88 |
| 2009/0082774 A1* | 3/2009 | Oti | A61B 17/15 606/87 |
| 2009/0087276 A1 | 4/2009 | Rose | |
| 2010/0160918 A1* | 6/2010 | Cuckler | A61B 17/1764 606/88 |
| 2011/0046629 A1 | 2/2011 | Green et al. | |
| 2014/0257309 A1 | 9/2014 | Aram et al. | |

FOREIGN PATENT DOCUMENTS

| | | |
|---|---|---|
| WO | 9730641 | 8/1997 |
| WO | 2012167016 | 12/2012 |
| WO | 2017007820 | 1/2017 |

OTHER PUBLICATIONS

"International Application Serial No. PCT/US2016/041137, Written Opinion dated Sep. 12, 2016", 6 pgs.

"European Application Serial No. 16741454.9, Response filed Sep. 27, 2018 to Office Action dated Mar. 21, 2018", 16 pgs.

* cited by examiner

FEMORAL FINISHING GUIDE

CLAIM OF PRIORITY

This application claims the benefit of U.S. Provisional Patent Application Ser. No. 62/189,416, filed on Jul. 7, 2015, the benefit of priority of which is claimed hereby, and which is incorporated by reference herein in its entirety.

FIELD

The present subject matter relates to orthopedic procedures and, more particularly, to bone resection apparatuses and methods for performing knee arthroplasties.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Knee prostheses can include a femoral component implanted on the distal end of the femur, which articulates with a tibial component implanted on the proximal end of a tibia to replicate the function of a healthy natural knee. Various types of arthroplasties are known including a total knee arthroplasty, where all of the articulating compartments of the joint are repaired with prosthetic components, and a unicompartmental knee arthroplasty, where only one damaged compartment of the knee is repaired with prosthetic components.

OVERVIEW

The present inventors recognize, among other things, an opportunity for reducing the likelihood for soft tissue damage occurring during resection of the femur. More particularly, the present inventors have recognized that projections along one or both of the lateral and medial side of a femoral finishing guide can act to capture a saw blade and direct it into a cutting slot. As such, the soft tissue can have a reduced likelihood in being contacted by the saw during the resection.

Furthermore, the present inventors have recognized that fixation of the femoral finishing guide to the femur can be improved by fixating the femoral finishing guide at an area of the cut guide that is as anterior as possible. Thus, the present inventors have developed an anterior flange with an anterior most fixation aperture that can receive a bone screw or other fastener therein. The present inventors have also recognized that the femoral finishing guide can include a boss or similar depth setting feature that can be used to set a desired bone removal depth for a peg of a prosthesis. In this way, rather than utilizing multiple bone removal tools having different lengths, a single bone removal tool can be utilized to achieve the desired depth even in instances where multiple peg holes are utilized by the implant.

To further illustrate the apparatuses and methods disclosed herein, the following non-limiting examples are provided:

Example 1 is an apparatus for guiding a femoral bone cut during knee replacement surgery, the apparatus comprising: a first side configured to interface with a resected surface of a femur; a second side spaced from the first side; one or more slots defined by the apparatus and extending from the first side to the second side; and a third side between the first side and the second side and having at least one projection extending therefrom, the at least one projection configured to guide a cutting tool into the one or more slots.

In Example 2, the subject matter of Example 1 optionally can include the at least one projection is defined by a portion of the second side.

In Example 3, the subject matter of any one or more of Examples 1-2 optionally can include the one or more slots comprise a posterior facet cut slot and a posterior chamfer cut slot.

In Example 4, the subject matter of any one or more of Examples 1-3 optionally can include the third side comprises one of a medial or lateral side of the apparatus.

In Example 5, the subject matter of any one or more of Examples 1-4 optionally can include the second side comprises: an anterior flange having one or more fixation apertures; and a boss disposed posterior of the anterior flange and having a first hole configured to receive a bone removal tool.

In Example 6, the subject matter of Example 5 optionally can include wherein the boss is configured to set a desired depth for the bone removal tool.

In Example 7, the subject matter of any one or more of Examples 5-6 optionally can further comprise a second fixation aperture disposed between the boss and the anterior flange, the second fixation aperture arranged oblique to the one or more fixation apertures of the anterior flange.

In Example 8, the subject matter of any one or more of Examples 5-7 optionally can include to an opening of the one or more slots is disposed between the anterior flange and the boss.

In Example 9, the subject matter of any one or more of Examples 5-8 optionally can include at least a second hole disposed posterior of the first hole, the second hole configured to receive the same bone removal tool as the first hole.

In Example 10, the subject matter of any one or more of Examples 1-9 optionally can include the at least one projection comprises a pair of anterior-posterior or proximal-distal spaced projections that form a capture.

In Example 11, the subject matter of Example 10 optionally can include at least one of the pair of projections that forms the capture has a taper from the second side toward the first side.

In Example 12, the subject matter of any one or more of Examples 10-11 optionally can include the taper terminates prior to the first side.

In Example 13, the subject matter of any one or more of Examples 10-12 optionally can include at least one of the pair of projections that form the capture includes a chamfered surface configured to guide the cutting tool into the one or more slots.

Example 14 is an apparatus for guiding a femoral bone cut during a unicompartmental knee replacement surgery, the apparatus comprising: a first side configured to interface with a resected distal surface of a single condyle of a femur; a second side spaced from the first side and including an anterior flange having one or more fixation apertures; a lateral side and a medial side disposed between the first side and the second side, at least one of the lateral side and the medial side having a pair of spaced apertures that project therefrom to form a capture; and at least one slot defined by the apparatus and extending from the first side to the second side, the at least one slot further extending toward at least one of the lateral side and the medial side and having an opening defined by the capture.

In Example 15, the subject matter of Example 14 optionally can include wherein the second side includes a boss disposed posterior of the anterior flange and having a first hole configured to receive a bone removal tool.

In Example 16, the subject matter of any one or more of Examples 14-15 optionally can include the at least one of the projections that form the capture defines a portion of the second side.

In Example 17, the subject matter of any one or more of Examples 14-16 optionally can include at least one of the projections that form the capture has a taper from the second side toward the first side.

In Example 18, the subject matter of Example 17 optionally can include wherein the taper terminates prior to the first side.

In Example 19, the subject matter of any one or more of Examples 14-18 optionally can include at least one of the projections that form the capture includes a chamfered surface configured to guide a cutting tool into the at least one slot.

In Example 20, the subject matter of any one or more of Examples 14-19 optionally can include the at least one slot comprises a posterior facet cut slot and a posterior chamfer cut slot, and wherein the capture comprises first and second captures, the first capture corresponding to the posterior facet cut slot and the second capture corresponding to the posterior chamfer cut slot.

Example 21 is a method of performing a femoral knee resection comprising: resecting a distal surface of at least a single condyle of a femur; positioning a cut guide on the resected distal surface, the cut guide configured to facilitate one or both of a posterior facet cut and a posterior chamfer cut; fixating the cut guide to the femur using an anterior portion of the cut guide; and resecting the femur by performing one or both of the posterior facet cut and the posterior chamfer cut utilizing the cut guide, the resecting aided by a pair of spaced apertures that form a capture that projects from at least one of a lateral side and a medial side of the cut guide.

In Example 22, the subject matter of Example 21 optionally can include adjusting a position of the cut guide with reference to one or more anatomical landmarks of the knee.

In Example 23, the subject matter of any one or more of Examples 21-22 optionally can further comprise fixating the cut guide the femur in a second location, the second location posterior to the anterior portion of the cut guide.

In Example 24, the subject matter of any one or more of Examples 21-23 optionally can further comprise removing bone from the femur to facilitate reception of a peg of an implant, the depth of the removing of bone set by a boss projecting from a surface of the cut guide.

In Example 25, the subject matter of Example 24 optionally can include removing bone from the femur at a second location to facilitate reception of a second peg of the implant, the removing utilizing a same bone removal tool as was used with the boss.

In Example 26, the apparatuses or method of any one or any combination of Examples 1-25 can optionally be configured such that all elements or options recited are available to use or select from.

These and other examples and features of the present apparatuses and methods will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to devices and methods that can be used in various knee procedures including a total knee replacement procedure (TKA), a cruciate retaining total knee procedure, a unicompartmental knee replacement procedure, a bicompartmental knee replacement procedure comprised of two unicompartmental knee replacements, a procedure that utilizes a single (total) femoral component and two unicompartmental tibial components, and other types of knee replacement procedures. The disclosed devices include a femoral cut guide (sometimes referred to as a femoral finishing guide, cut guide, guide or apparatus herein) having one or both of a lateral and/or medial side that can include projections that can define one or more captures for facilitating resection of the femur while protecting soft tissue from contact with the cutting tool. According to further examples, the femoral cut guide can include additional features that can reduce surgical time and/or complexity.

Figure 1A:
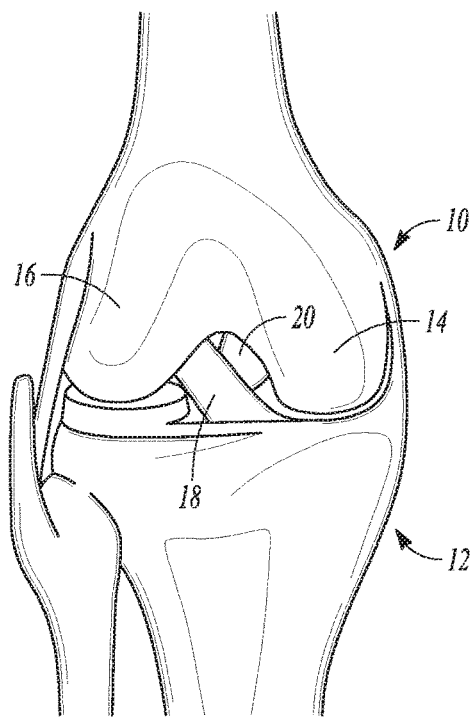
FIG. 1A is an anterior view of a natural femur and tibia according to an example of the present application.
Figure 1B:
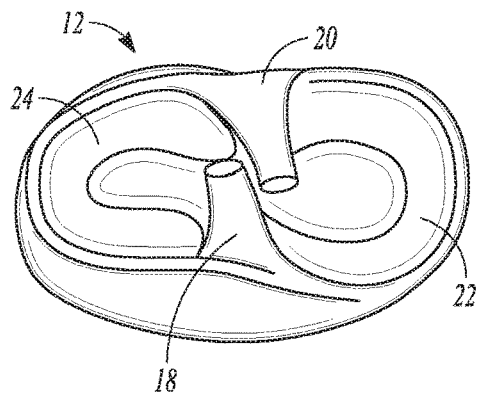
FIG. 1B is a top view of the tibia of FIG. 1A according to an example of the present application.

FIG. 1A illustrates a natural femur 10 and tibia 12. The femur 10 can include medial 14 and lateral 16 condyles at a distal end of the femur 10. Various ligaments can be attached to the femur 10 and/or the tibia 12. An anterior cruciate ligament (ACL) 18 can extend from an anterior side of the tibia 12 to the femur 10, and a posterior cruciate ligament (PCL) 20 can extend from a posterior side of the tibia 12 to the femur 10. FIG. 1B is a top view of the tibia 12 and further illustrates some of these ligaments as well as a medial meniscus 22 and a lateral meniscus 24 that are located between the tibia 12 and the medial 14 and lateral 16 condyles.

Figure 1C:
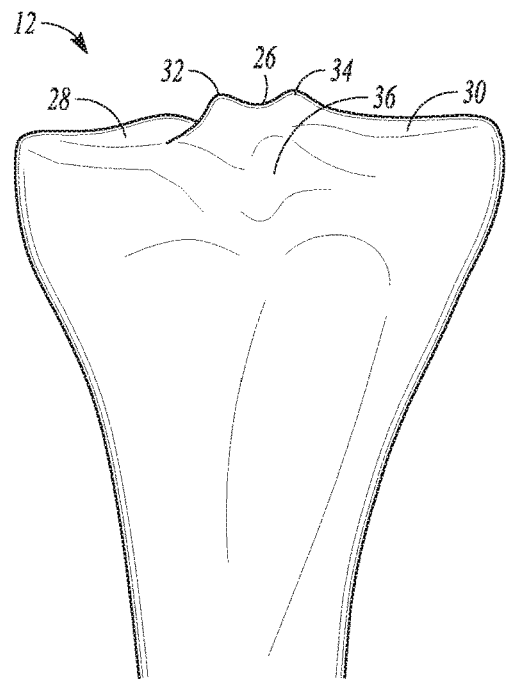
FIG. 1C is an anterior view of the tibia of FIGS. 1A and 1B, with the anatomical features shown in FIG. 1B removed according to an example of the present application.

FIG. 1C illustrates a posterior side view of the tibia 12 with the ligaments and other anatomical features shown in FIG. 1B removed. The tibia 12 can include an intercondylar eminence 26, which is a bony elevation or raised area between a medial articular surface 28 and a lateral articular surface 30 at a proximal end of the tibia 12. The intercondylar eminence 26 can include medial 32 and lateral 34 tubercles extending from the intercondylar eminence 26. The ACL 18 and PCL 20 are attached to the tibia 12 at locations anterior and posterior, respectively, to the intercondylar eminence 26. For reference, the PCL 20 is attached to the tibia 12 at a location 36 on a posterior end of the tibia 12.

In a unicompartmental knee replacement procedure (sometimes referred to as a "unicondylar" knee replacement procedure or "UKA") one of the medial 14 and lateral 16 condyles of the femur 10 are resected. Further resection is performed to remove one of the medial articular surface 28 and the lateral articular surface 30 of the tibia 12. Femoral cutting apparatuses can be utilized to remove corresponding articular surfaces of the femur 10 that would otherwise interface with either the medial articular surface 28 or the lateral articular surface 30. Prostheses can be implanted on the femur 10 and the tibia 12 providing for the replaced articular surfaces. Other portions of the knee, e.g., the intercondylar eminence 26, ACL 18, and PCL 20 can be maintained in the UKA. In a bicompartmental knee replacement procedure, both the medial 14 and lateral 16 condyles are resected and the medial articular surface 28 and the lateral articular surface 30 are also resected. Similar to a unicompartmental knee replacement procedure, the bicompartmental knee replacement procedure maintains portions of the knee such as the intercondylar eminence 26. Similarly, a knee replacement procedure that could utilize a total femoral component and two unicompartmental tibial components can seek to maintain portions of the knee such as the intercondylar eminence 26.

As used herein, "proximal" refers to a direction generally toward the torso of a patient, and "distal" refers to the opposite direction of proximal, i.e., away from the torso of a patient. As the resections described herein are generally performed with the knee in flexion, "distal" refers to a direction generally facing away from the patient, i.e. toward the surgeon performing the surgery, and "proximal" refers to the opposite direction of distal, i.e., toward the distal surface of the femur. As used herein, the terms "anterior" and "posterior" should be given their generally understood anatomical interpretation. Thus, "posterior" refers to a rear of the patient, e.g., a back of the knee. Similarly, "anterior" refers to a front of the patient, e.g., a front of the knee. Thus, "posterior" refers to the opposite direction of "anterior".

In the context of cutting apparatus such as those disclosed herein, such directions correspond to the orientation of the apparatus when in use (i.e. when mounted to or positioned adjacent the patient in an operable position to make desired resections with the knee joint in flexion). As such, the proximal side of the cutting apparatus is that side which will ordinarily be closest to the torso of the patient, the distal side closest to the surgeon, the posterior of the apparatus generally closest to the tibia, etc.

Figure 2:
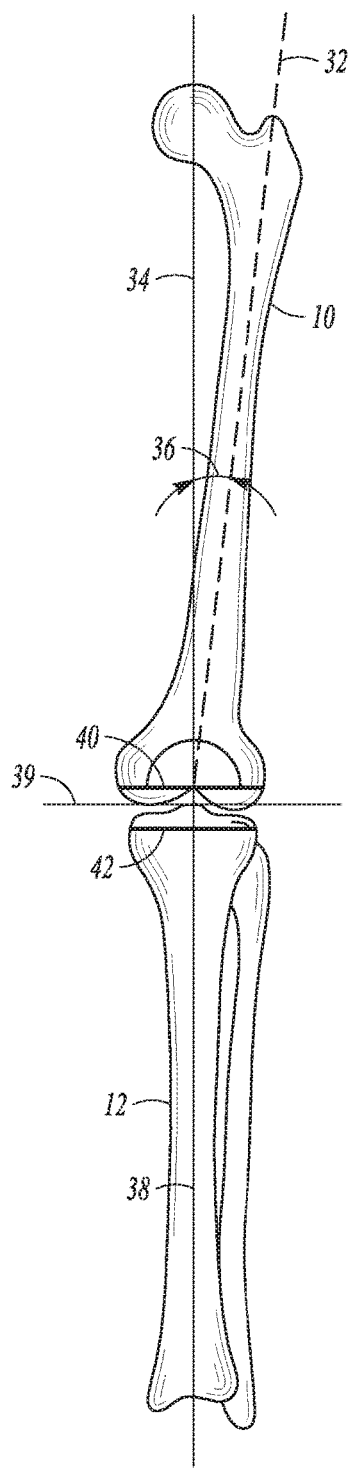
FIG. 2 is a front elevation view of a tibia and a femur showing axes of the knee joint according to an example of the present application.
Figure 3:
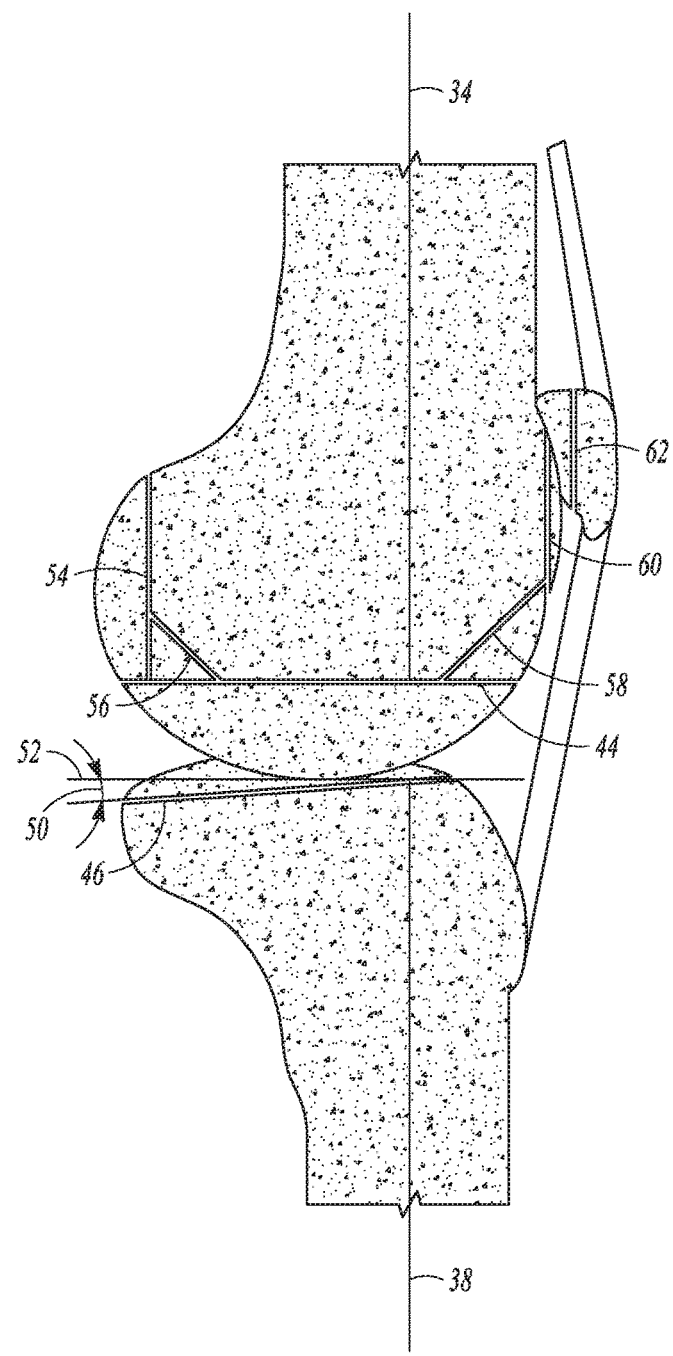
FIG. 3 is a side section view of a knee joint showing typical bone cuts used in replacing the joint surfaces according to an example of the present application.
Figure 4:
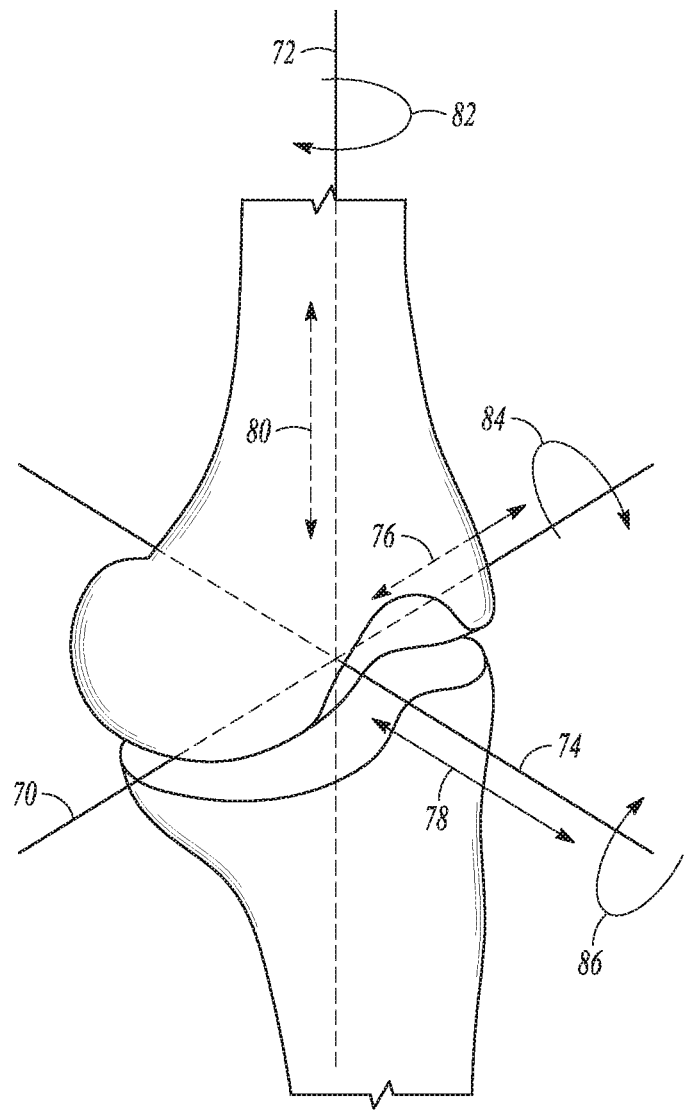
FIG. 4 is a perspective view of the knee joint showing aspects of component positioning according to an example of the present application.

FIGS. 2-4 illustrate several aspects of implant orientation. FIG. 2 illustrates various axes of the lower limb in the frontal plane. Axes can be defined for each segment of the lower limb. For example, the femur 10 has an anatomic axis 32 coinciding generally with its intramedullary canal. It also has a mechanical axis 34, or load axis, running from the center of the femoral head to the center of the knee. The angle 36 between these two axes 32, 34 in the frontal plane varies within the patient population but is on the order of 4-9°. The two axes 32, 34 are approximately superimposed in the sagittal plane (FIG. 3). Likewise, the tibia 12 has a mechanical axis 38 coinciding generally with its intramedullary canal. The mechanical axis 38 of the tibia 12 runs from the center of the knee to the center of the ankle. The transverse axis, or joint line 38, about which the knee flexes, is parallel to a line through the medial and lateral femoral condyles and parallel to the tibial plateau. Typically, the distal femur and proximal tibia are resected to be parallel to the joint line 39, and thus perpendicular to the mechanical axes 34, 38 as indicated at 40 and 42. The intersection of the femoral and tibial mechanical axes 34, 38 may subtend a small angle relative to one another. However, the angle can be small such that the axes 34, 38 are approximately collinear and may be treated as collinear for most purposes.

FIG. 3 illustrates the knee joint from the side or sagittal view and various bone cuts that may be made to align implant components. The distal femoral cut 44 is typically made perpendicular to the femoral axes 32, 34 in the sagittal plane. The proximal tibial resection 46 is typically cut to match the natural posterior slope, or rotation, of the proximal tibia relative to the mechanical axes 34, 38. The amount of posterior to anterior slope 50 relative to a reference line 52 perpendicular to the mechanical axes 34, 38 varies in the patient population but is on the order of 5° to 7°. The distance between the distal femoral cut 44 and proximal tibial cut 46 along the mechanical axes 34, 38 is the extension gap. Other cuts may be made depending on the components that are to be implanted. These include a posterior femoral cut 54, a posterior femoral chamfer cut 56, an anterior femoral chamfer cut 58, an anterior femoral cut 60, and a tibial sagittal cut (not shown in FIG. 3). The patella 62 may also be cut to allow for replacement of the patellar articular surface.

As described above, in a unicompartmental knee replacement procedure, only the medial or lateral side of the knee joint is resurfaced. Furthermore, the trochlear, or patellar bearing, surface of the femur is typically left intact. Unicompartmental implant designs vary, but typically only the distal femoral cut 44, the femoral chamfer cut 56 and posterior femoral cut 54 are needed to accommodate the unicompartmental femoral implant.

FIG. 4 depicts six aspects of component positioning relative to a coordinate system in which the x-axis 70 corresponds approximately to the joint line 39, the z-axis 72 corresponds approximately to the mechanical axes 34 and 38, and the y-axis 74 is normal to the other two. Position along each of these axes is depicted by arrows. Position along the x, y, and z axes determines the medial/lateral (dx) 76, anterior/posterior (dy) 78, and proximal/distal (dz) 80 positioning of components respectively. Rotation about each of these axes is also depicted by arrows. Rotation about the z-axis (rz) 82 corresponds anatomically to external rotation of the femoral component, rotation about the x-axis (rx) 84 corresponds to extension plane rotation, and rotation about the y-axis (ry) 86 corresponds to varus/valgus rotation.

Figure 5:
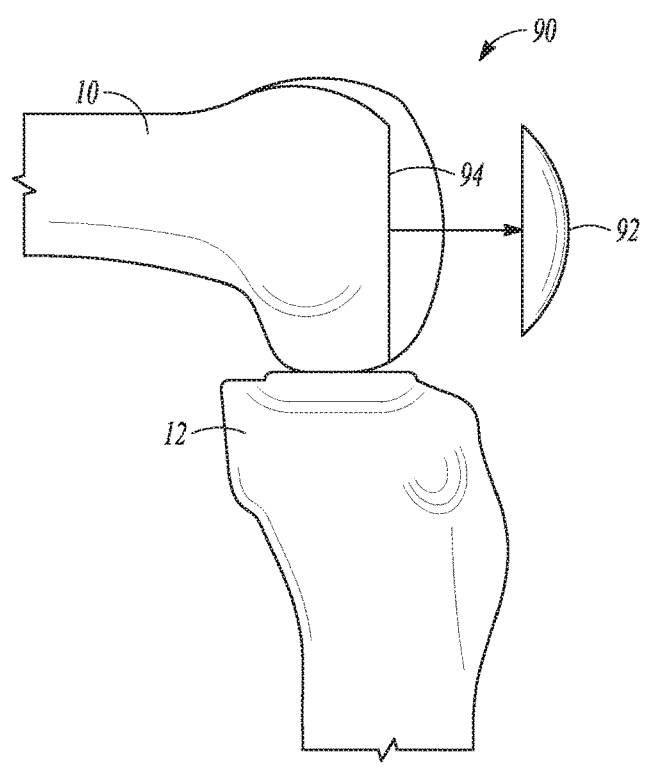
FIG. 5 is a side view of the knee joint with one of the femoral condyles resected according to an example of the present application.

FIG. 5 shows a knee joint 90 including a distal portion of the femur 10 and a proximal portion of the tibia 12. The procedure illustrated is shown in reference to a unicompartmental knee surgery in which a single compartment of the knee joint 90 is replaced including a portion of one femoral condyle and a portion of the proximal tibia 12. However, it is contemplated that apparatuses and methods according to the present application may also be used in other types of knee replacements, in which both the medial and lateral portions of the knee are resurfaced. In FIG. 5, a distal femoral cut (such as distal femoral cut 44 of FIG. 3) to the femur 10 has been performed. As such, a distal portion 92 of a single femoral condyle has been resected using conventional techniques such as guiding a saw blade to resect the portion 92 while the knee is in flexion. This resection leaves a resected distal surface 94 of the single condyle.

Figure 5A:
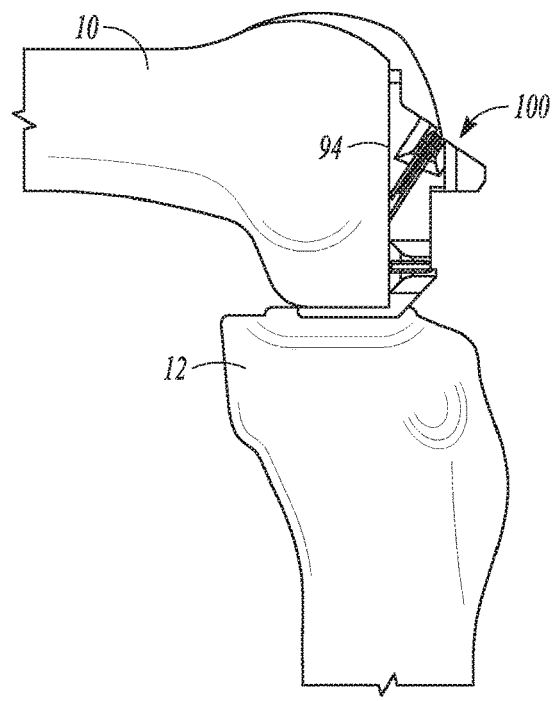
FIG. 5A is a side view of the knee joint of FIG. 5 with a femoral cut guide mounted to the resected condyle according to an example of the present application.

FIG. 5A shows a femoral cut guide 100 positioned on the resected distal surface 94 of the single condyle of the femur 10. The cut guide 100 extends between a posterior portion of the femur 10 and an anterior portion of the femur 10. As will be discussed in further detail subsequently, the cut guide 100 can be configured to facilitate one or both of a posterior facet cut and a posterior chamfer cut (e.g., posterior femoral cut 54 and/or posterior femoral chamfer cut 56 of FIG. 3). The configuration of the cut guide 100 can aid in protecting soft tissue either medial to and/or lateral to and adjacent the resected distal surface 94. The cut guide 100 can also be configured to facilitate removing bone from the femur 10 for reception of one or more pegs of an implant (not shown) as will be discussed in further detail subsequently.

Figure 6A:
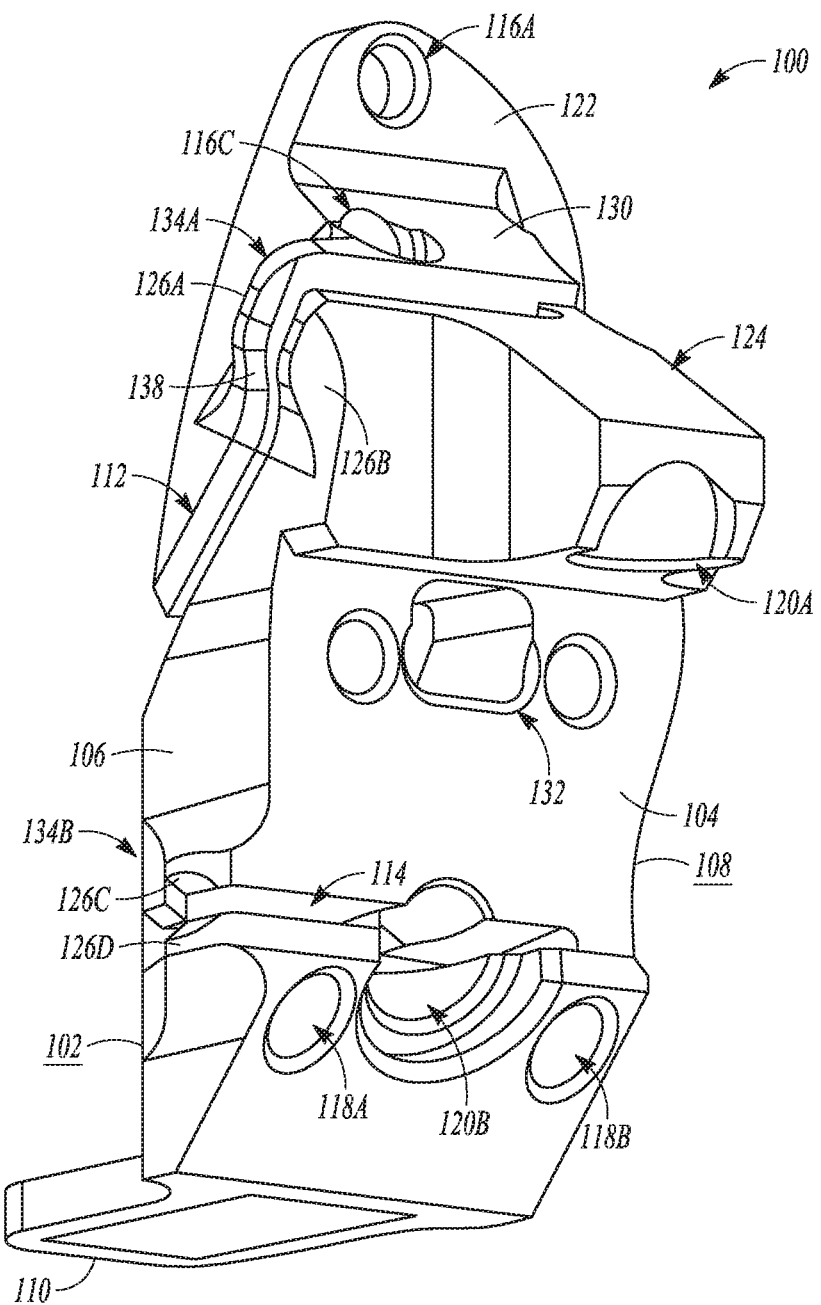
FIG. 6A to 6C are perspective views of the femoral cut guide of FIG. 5A according to examples of the present application.
Figure 6B:
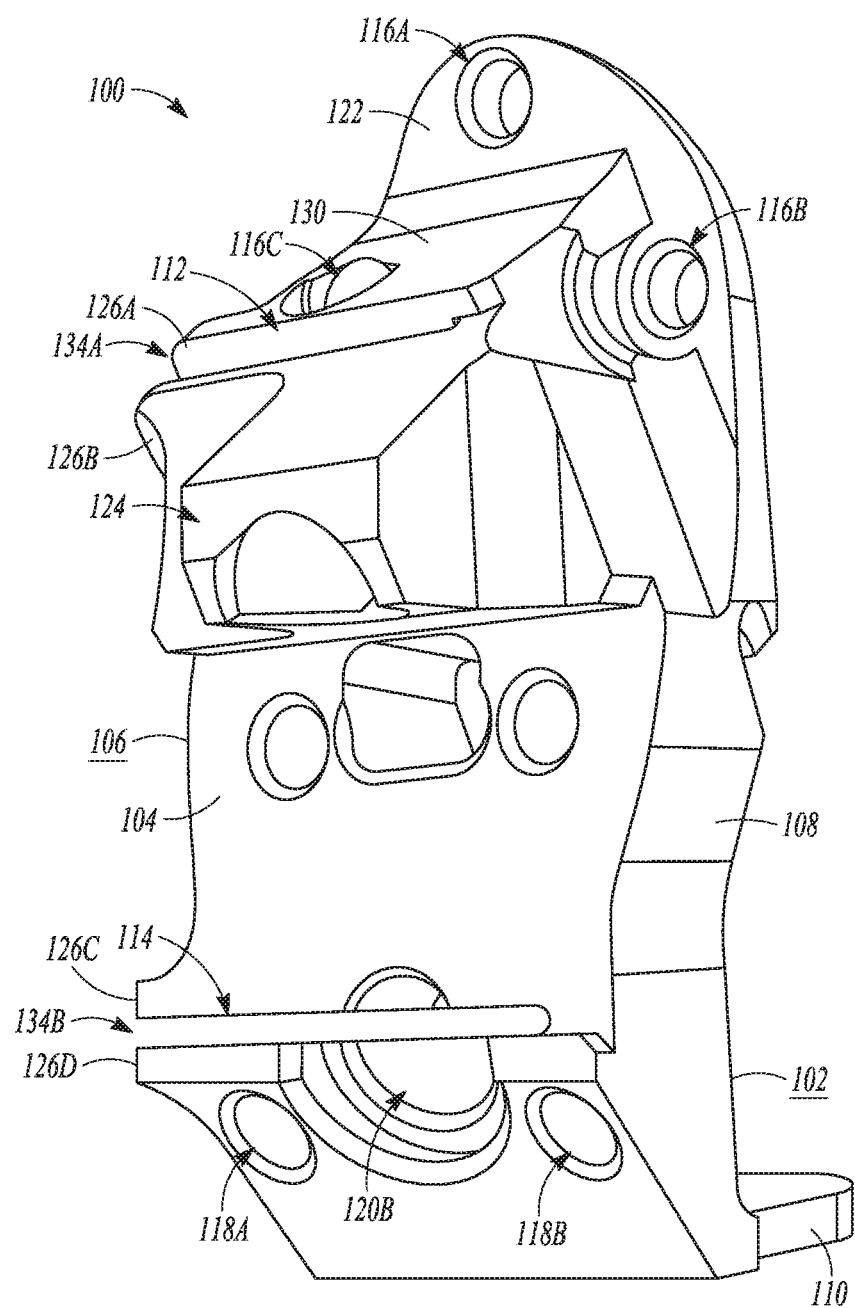
Figure 6C:
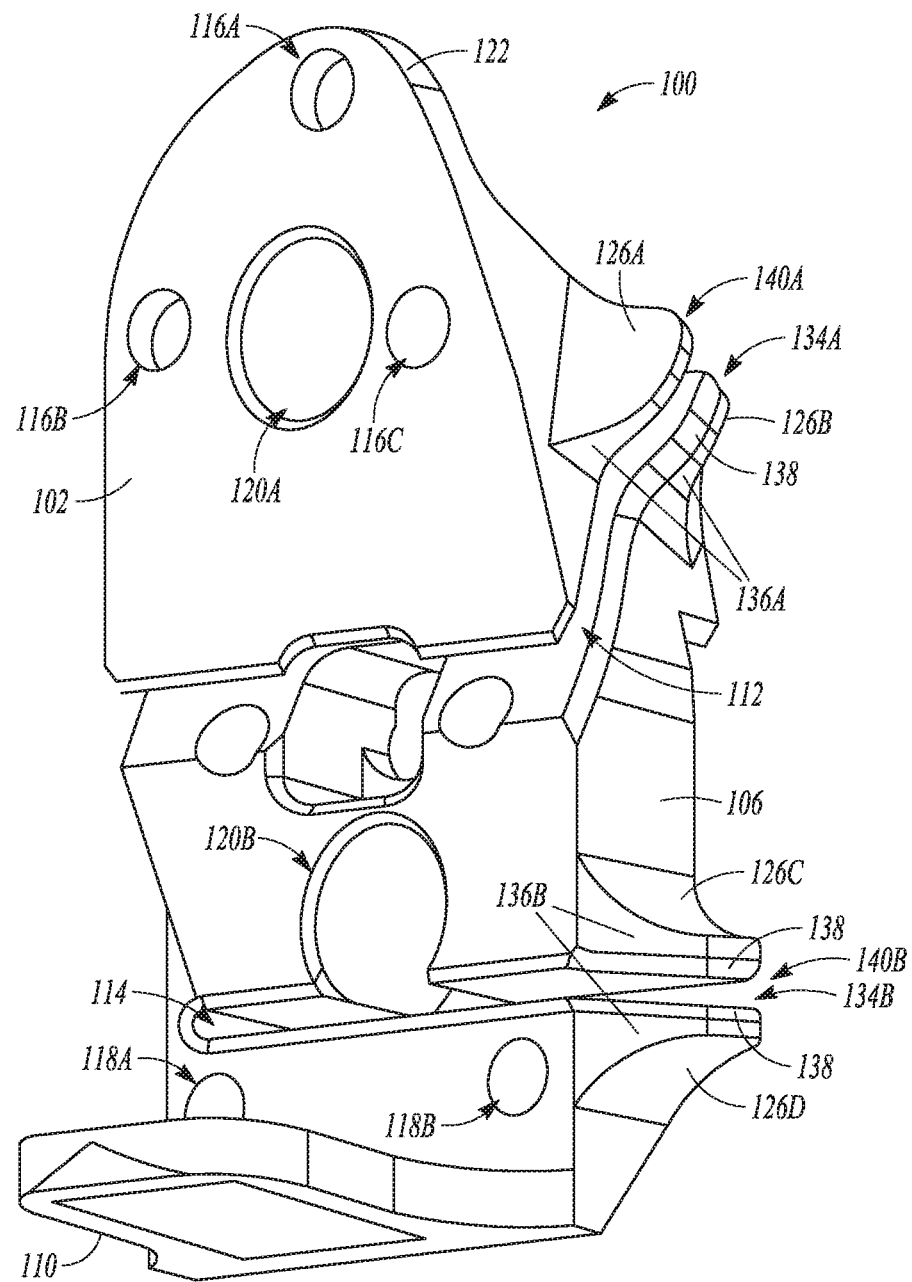
Figure 7A:
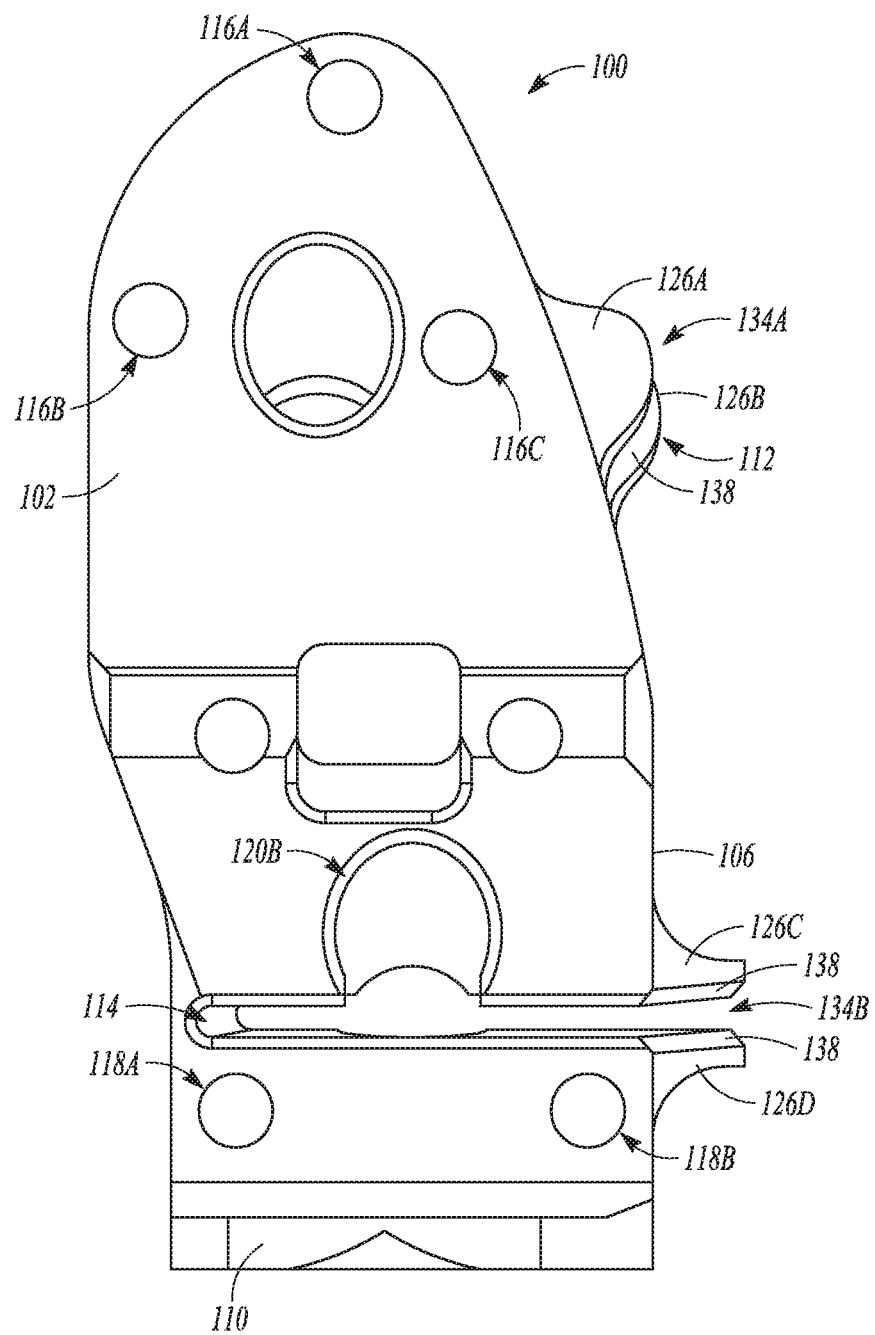
FIG. 7A is a plan view of a proximal side of the femoral cut guide of FIGS. 5A to 6C according to an example of the present application.
Figure 7B:
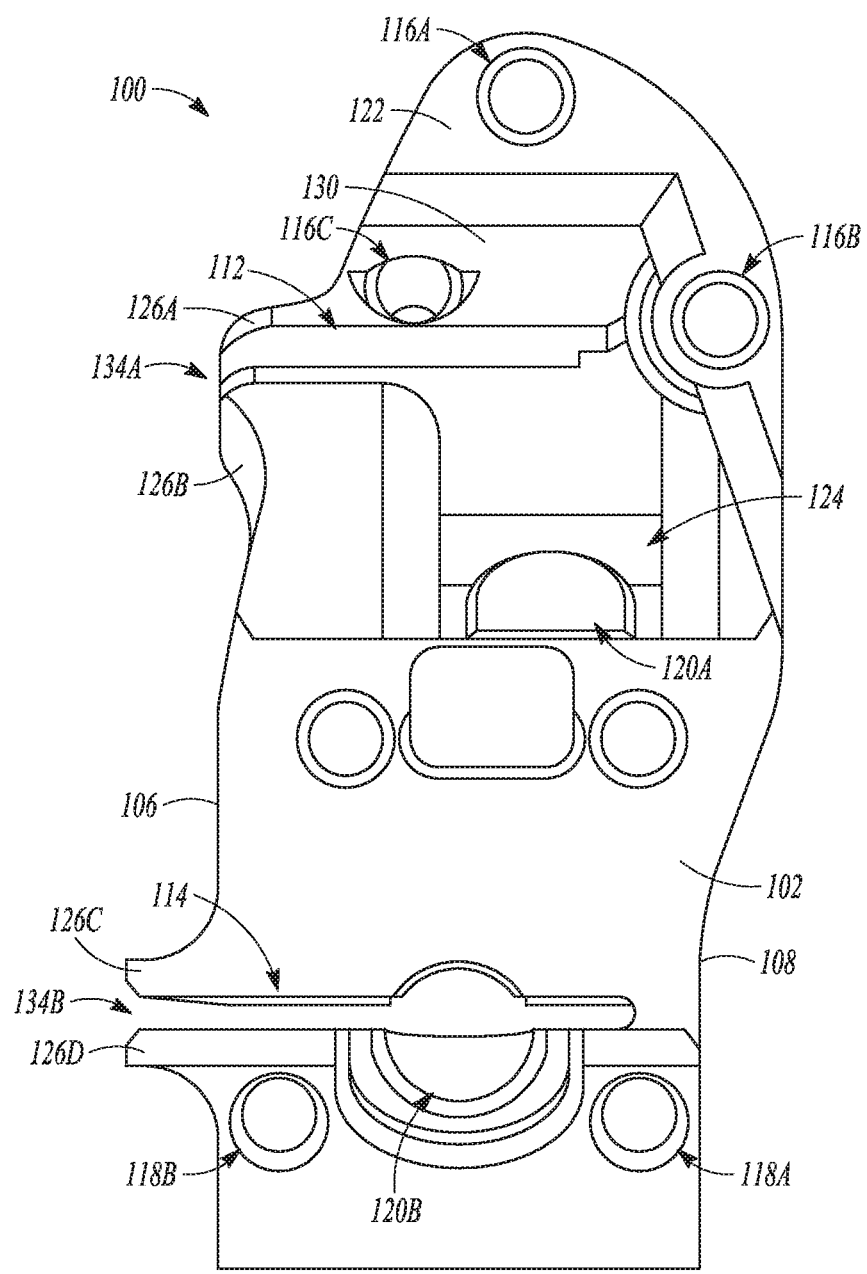
FIG. 7B is a plan view of a distal side of the femoral cut guide of the FIGS. 5A to 6C according to an example of the present application.
Figure 7C:
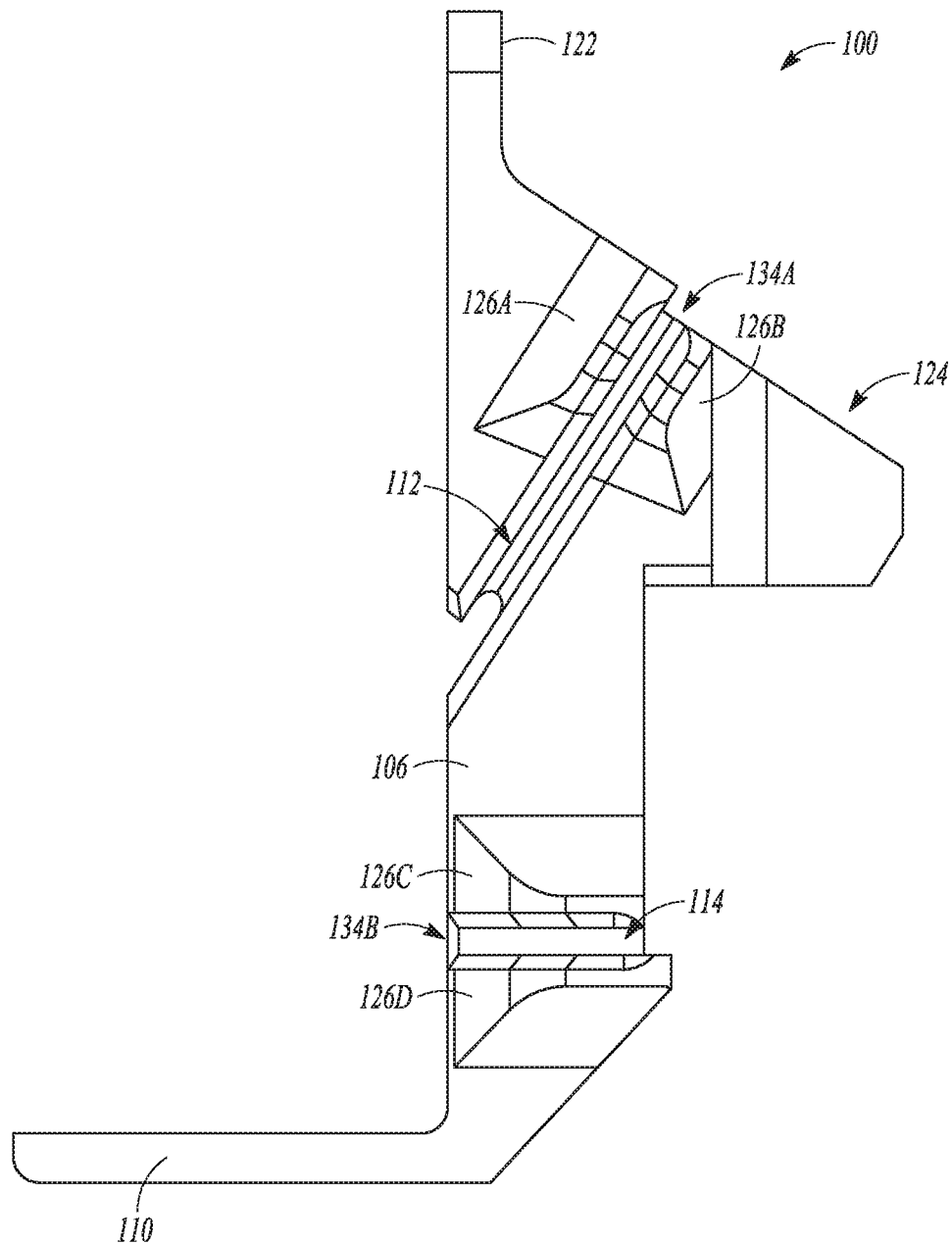
FIG. 7C is a plan view of a lateral side of the femoral cut guide of the FIGS. 5A to 6C according to an example of the present application.
Figure 7D:
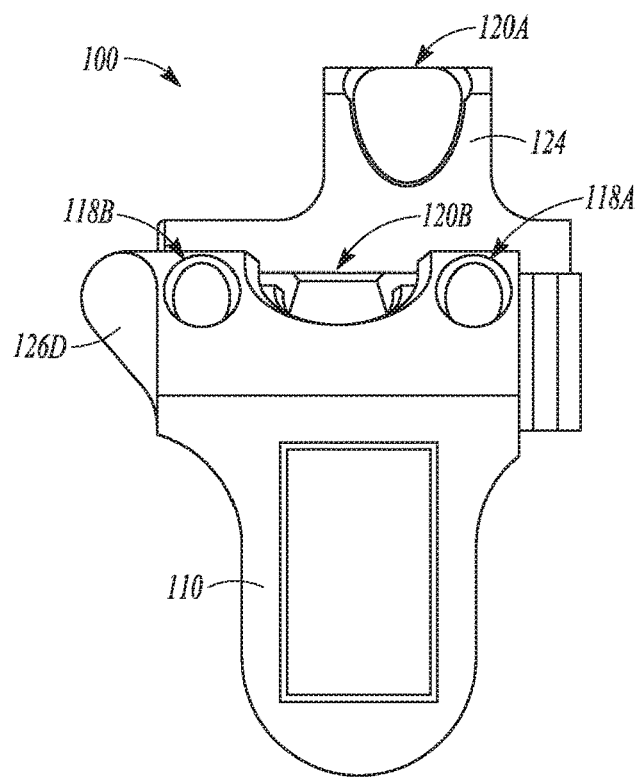
FIG. 7D is a plan view of a posterior side of the femoral cut guide of the FIGS. 5A to 6C according to an example of the present application.
Figure 7E:
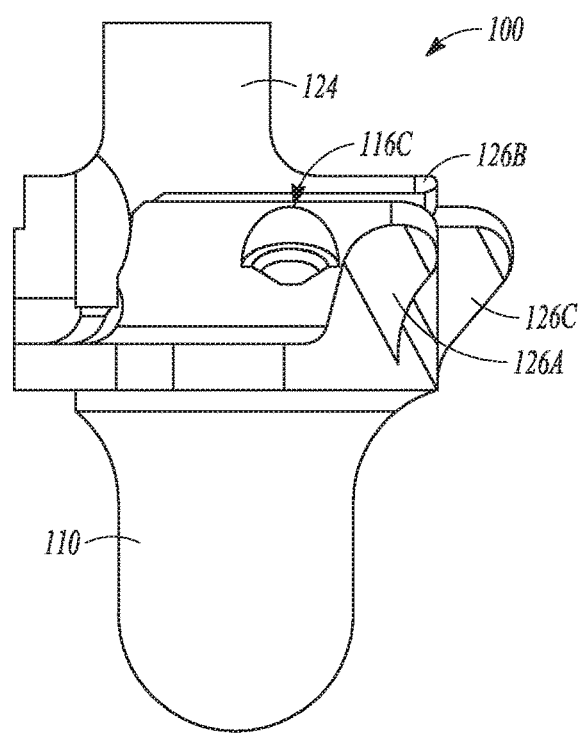
FIG. 7E is a plan view of an anterior side of the femoral cut guide of the FIGS. 5A to 6C according to an example of the present application.

FIGS. 6A-6C are perspective views of the femoral cut guide 100 according to an example of the present application with the cut guide 100 removed from adjacent the knee. FIGS. 7A-7E show sides the femoral cut guide 100 in plan views. As shown in various of the FIGURES, the cut guide 100 can include a first side 102, a second side 104, a third side 106, a fourth side 108, a foot 110, a first slot 112, a second slot 114, anterior fixation apertures 116A, 116B, 116C, posterior fixation apertures 118A and 118B, and holes 120A and 120B. The second side 104 can include features such as an anterior flange 122 and a boss 124. The third side 106 can include projections 126A, 126B, 126C, and 126D.

According to the example shown, the proximal first side 102 is arranged to generally oppose the distal second side 104. Thus, the second side 104 is spaced from the first side 102 by a thickness of the cut guide 100. The third side 106 and the fourth side 108 can generally oppose one another and can extend between the first side 102 and the second side 104. The cut guide 100 can be configured such that on a right knee the cut guide 100 can be utilized to make resections on the lateral condyle of the femur. The same cut guide, cut guide 100, can also be utilized to make resections on the medial condyle of a left knee. A second guide (not shown) having inverted medial-lateral geometry from that of cut guide 100 can be utilized to address resections to the medial condyle of the right knee and/or the lateral condyle of the left knee as desired. Thus, depending on the condyle being resected the third side 106 can comprise either a medial side of the guide (for example guide 100) or a lateral side of the guide. The third side 106 can face away from the second condyle of the femur.

The foot 110 can be disposed at a posterior end of the cut guide 102 and can extend generally proximally away from the remainder of the guide 102. During use, the foot 110 can be configured to interface with an un-resected posterior portion of the condyle of the femur prior to resection utilizing the cut guide 100 as shown in FIG. 5A.

The first slot 112 and the second slot 114 can be defined by the cut guide 100 and can extend from the first side 102 to the second side 104 (having openings to either side) through the guide 100. The slots 112 and 114 can further be defined to extend toward the third side 106 (at least one of the lateral side and the medial side of the cut guide depending upon the condyle being resected). The anterior fixation apertures 116A, 116B, and 116C, the posterior fixation apertures 118A and 118B, and the holes 120A and 120B can be defined by the cut guide 100 and can extend from the first side 102 to the second side 104 through the guide 100.

The anterior fixation apertures 116A, 116B, and 116C can be arranged along an anterior portion of the cut guide 100 such as along the anterior flange 122. More particularly, the fixation apertures 116A and 116B can be defined by the anterior flange 122. The anterior most fixation aperture 116A can be spaced from the more posterior second fixation aperture 116B. The third fixation aperture 116C can be disposed between the anterior flange 122 and the boss 124 on an angled surface 130 of the second side 104. The third fixation aperture 116C can be disposed just anterior of the first slot 112. According to the example, the third fixation aperture 116C can be angled with respect to either the anterior most fixation aperture 116A and/or the more posterior second fixation aperture 116B. Thus, according to some examples, the third fixation aperture 116C can be oblique to the to the one or more fixation apertures 116A, 116B of the anterior flange 122. Posterior fixation apertures 118A and 118B can be arranged on a posterior most portion of the cut guide 100 adjacent the foot 112.

As shown in the illustrated example, the second side 104 can include the boss 124 extending distally therefrom. The boss 124 can have the hole 120A extending therethrough in both proximal-distal and anterior-posterior directions. According to the example shown, the slot 112 can be disposed anterior of the boss 124 and can extend along the angled surface 130. The slot 112 can intersect with the hole 120A and can have and opening that is disposed between the anterior flange 122 and the boss 124.

In the example shown, one or more coupling elements 132 can be included with the cut guide 100. The coupling elements 132 can be disposed posterior of the boss 124 on the second side 104 and can be configured to facilitate coupling with another instrument such as an insertion handle, a sizing plate, a referencing sizer, for example. Such instruments can include the Zimmer Insertion Handle, Part No. 00-5843-054-00.

The hole 120B can be disposed to the posterior of the boss 124 and posterior of hole 120A and can be disposed adjacent the posterior fixation apertures 118A and 118B. The slot 114 can extend in substantially a proximal-distal direction through the cut guide 100 (in addition to the medial-lateral direction) and can be intersected by the hole 120A (which extends in both proximal-distal and posterior-anterior directions) according to some examples.

The projections 126A, 126B, 126C, and 126D can extend from the third side 106, and in some examples, can additionally be defined by a portion of the second side 104. According to the example of the FIGURES, the projections 126A, 126B can comprise a pair 134A of projections that are spaced anterior-posterior and proximal-distal from one another to form a capture at a lateral opening of the slot 112. Similarly, the projections 126C, 126D can comprise a pair 134B of projections that are spaced anterior-posterior from one another to form a capture at a lateral opening of the slot 114. At least one or both of the pair 134A of projections can have a taper 136A (FIG. 6C) from the second side 104 toward the first side 102. Similarly, at least one or both of the pair 134B of projections can have a taper 136B (FIG. 6C) from the second side 104 to the first side 102. The taper 136A and/or 136B can terminate prior to the first side 102. According to further examples, at least one of the projections of the pairs 134A and/or 134B can include a chamfered surface 138 configured to guide a cutting tool into the slot(s) 112 and/or 114.

According to one example, the first side 102 can be configured to interface with a resected surface (e.g., distal surface 94) of a femur. Features such as the first slot 112, the second slot 114, the anterior fixation apertures 116A, 116B, 116C, the posterior fixation apertures 118A and 118B, and the holes 120A and 120B extend through the cut guide 100 and are configured to receive various devices used in performance of the knee replacement procedure described herein.

The projections 126A, 126B, 126C, and 126D can be configured to capture and guide a cutting tool (e.g., a bone saw) into the one or more of the slots 112 and/or 114 via lateral openings 140A and 140B (FIG. 6C), respectively. The first slot 112 can comprise a posterior chamfer cut slot used to facilitate the posterior femoral chamfer cut 56 (FIG. 3). The second slot 114 can comprise a posterior facet cut slot used to facilitate the posterior femoral cut 54 (FIG. 3). Anterior fixation apertures 116A, 116B, 116C and posterior fixation apertures 118A and 118B can be configured to receive bone screws to mount the cut guide 100 to the femur as desired.

The cut guide 100 can also be utilized to facilitate the creation of peg holes in the femur. In particular, the holes 120A and 120B are configured to receive a bone removal tool such as a drill. The boss 124 can set a desired depth for the bone removal tool with respect to the hole 120A such that bone of the femur is removed as desired. According to some examples, the second hole 120B can be configured to receive the same bone removal tool as the first hole 120A. However, the depth of bone removal facilitated by the second hole 120B may differ from that of the first hole 120A, the desired depth being set by the features of the cut guide 100 such as the boss 124, a counter-bore, etc.

The cut guide 100 and other cut guides and instruments not specifically illustrated can be utilized to perform one or more femoral resections according to the method described below. For example, the method can resect a distal surface of at least a single condyle of a femur, position a cut guide on the resected distal surface (the cut guide configured to facilitate one or both of a posterior facet cut and a posterior chamfer cut), fix the cut guide to the femur using an anterior portion of the cut guide (e.g., using anterior fixation aperture 116A), and resect the femur by performing one or both of the posterior facet cut and the posterior chamfer cut utilizing the cut guide (the resecting aided by a pair of spaced apertures that form a capture that projects from at least one of a lateral side and a medial side of the cut guide).

According to some examples, evaluation of the profile of the cut guide relative to the resected distal surface of the tibia can be performed prior to fixing the cut guide thereto. The method can adjust a position of the cut guide with reference to one or more anatomical landmarks of the knee (e.g., the cut guide can be rotated such that all parts of the cut guide slightly spaced from edges of the resected distal surface of the femur, the guide can be adjusted such that the posterior facet cut can be generally parallel with a tibial cut in the frontal plane, etc.). In further examples, the method can fix the cut guide the femur in a second location, the second location posterior to the anterior fixation point of the cut guide. For example such fixation can utilize one or more of the anterior fixation apertures 116B and/or 116C and/or the posterior fixation apertures 118A and/or 118B as desired. According to further examples, the method can remove bone from the femur to facilitate reception of a peg of an implant. In some cases, the depth of the removal of bone can be set by a projection (e.g., boss 124) extending from a distal surface of the cut guide. According to other examples, the depth can be set by another feature such as a counter-bore within one of the holes (e.g., the hole 120B). In further examples, the method can remove bone from the femur at a second location to facilitate reception of a second peg of the implant. The second removal can utilize a same bone removal tool as was used with the first removal as the cut guide can be configured to set the removal depth desired for each removal so as to accommodate the peg received therein.

Figure 8:
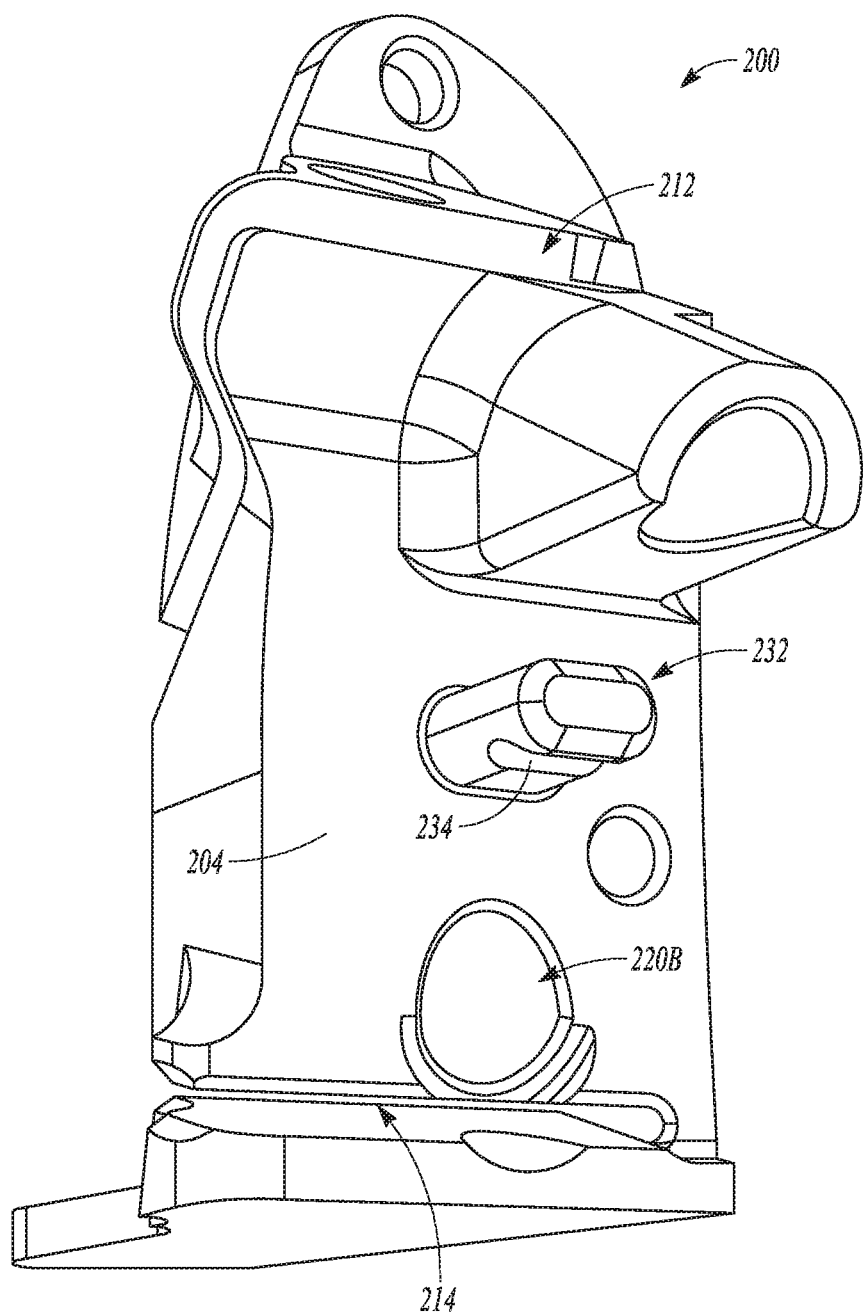
FIG. 8 is a perspective view of another femoral cut guide according to an example of the present application.

In FIG. 8, another example of a femoral cut guide 200 is shown. The femoral cut guide 200 can be constructed in a manner similar to that of cut guide 100, and thus, a detailed discussion of all of the features and components of the femoral cut guide 200 previously discussed in reference to the femoral cut guide 100 is not presented herein. The femoral cut guide 200 can include a distal side 204, a first slot 212, a second slot 214, a hole 220B and a coupling element 232. The coupling element 232 can include a groove 234.

According to the example of FIG. 8, the distal side 204 can have the slots 212 and 214 extending thereto. The slots 212 and 214 can be defined in the manner of slots 112 and 114 previously discussed. However, in the example of FIG. 8, the hole 220B (for peg creation) can be further offset from slot 214 such that the two intersect to a lesser extent than slot 114 and hole 120B.

The coupling element 232 of FIG. 8 can comprise a male projection from distal side 204. The groove 234 can be located along a side of the coupling element 232. The groove 234 can provide a detent or catch for a tool that is used to place and/or remove the femoral cut guide 200 from the femur (not shown). The coupling element 232 can be received in a complementary female recess in the tool.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. An apparatus for guiding a femoral bone cut during a unicompartmental knee replacement surgery, the apparatus comprising:
   a first side configured to interface with a resected surface created by removal of only a single condyle of a femur;
   a second side spaced from the first side and having a boss projecting therefrom with a first hole therein configured to receive a bone removal tool to create a stem aperture in the femur, wherein the stem aperture is located at the resected surface of the femur;
   one or more slots defined by the apparatus and extending from the first side to the second side; and
   a third side between the first side and the second side and having at least a first pair of spaced apart projections extending therefrom, the first pair of spaced apart projections configured to form a capture to guide a cutting tool into one of the one or more slots, wherein the first pair of projections comprise one of anterior-posterior or proximal-distal spaced projections, and wherein the first pair of projections has a taper from the second side toward the first side.

2. The apparatus of claim 1, wherein the one or more slots comprise a posterior facet cut slot and a posterior chamfer cut slot.

3. The apparatus of claim 1, wherein the third side comprises one of a medial or lateral side of the apparatus.

4. The apparatus of claim 1, wherein the second side comprises:
   an anterior flange having one or more fixation apertures.

5. The apparatus of claim 4, wherein the boss is configured to set a desired depth for the bone removal tool.

6. The apparatus of claim 4, further comprising a second fixation aperture disposed between the boss and the anterior flange, the second fixation aperture arranged oblique to the one or more fixation apertures of the anterior flange.

7. The apparatus of claim 4, wherein an opening of the one or more slots is disposed between the anterior flange and the boss.

8. The apparatus of claim 4, further comprising at least a second hole disposed posterior of the first hole, the second hole configured to receive the same bone removal tool as the first hole.

9. The apparatus of claim 1, wherein the taper terminates prior to the first side.

10. An apparatus for guiding a femoral bone cut during a unicompartmental knee replacement surgery, the apparatus comprising:
    a first side configured to interface with a resected distal surface of only a single condyle of a femur;
    a second side spaced from the first side and including an anterior flange having one or more fixation apertures;
    a lateral side and a medial side disposed between the first side and the second side, the lateral side having a first pair of spaced projections that project therefrom and are configured to form a first capture and having a second pair of spaced projections that project therefrom and are configured to form a second capture;
    a first slot defined by the apparatus and extending from the first side to the second side, the first slot further extending to the lateral side and having an opening defined by the first capture, whereby the first capture is configured to guide a cutting tool into the first slot; and
    a second slot defined by the apparatus and extending from the first side to the second side, the second slot further extending to the lateral side and having an opening defined by the second capture, whereby the second capture is configured to guide the cutting tool into the second slot.

11. The apparatus of claim 10, wherein the second side includes a boss disposed posterior of the anterior flange and having a first hole configured to receive a bone removal tool.

12. The apparatus of claim 10, wherein the first and second pair of projections each e has a taper from the second side toward the first side.

13. The apparatus of claim 12, wherein the taper terminates prior to the first side.

14. The apparatus of claim 10, wherein the first slot and the second slot comprises a posterior facet cut slot and a posterior chamfer cut slot.

* * * * *